United States Patent [19]

Szpur

[11] 3,981,304
[45] *Sept. 21, 1976

[54] DISPENSING AND APPLICATING DEVICE AND PRODUCTION OF SAME

[76] Inventor: Roman Szpur, 2685 Culver Ave., Kettering, Ohio 45429

[ * ] Notice: The portion of the term of this patent subsequent to July 29, 1992, has been disclaimed.

[22] Filed: June 11, 1975

[21] Appl. No.: 585,876

Related U.S. Application Data

[63] Continuation-in-part of Ser. No. 486,463, July 8, 1974, Pat. No. 3,896,808.

[52] U.S. Cl. ............................... 128/269; 401/133; 222/81; 222/213
[51] Int. Cl.² ........................................ A61M 35/00
[58] Field of Search .......... 128/272, 269, 216, 270, 128/2 W, 218 M; 222/81, 82, 83, 87, 213, 214; 15/244; 401/134, 160, 133

[56] References Cited
UNITED STATES PATENTS

| | | | |
|---|---|---|---|
| 2,361,647 | 10/1944 | Nyden | 222/214 |
| 2,543,195 | 2/1951 | Petion | 222/213 X |
| 2,642,065 | 6/1953 | Negri | 128/269 |
| 2,726,656 | 12/1955 | Lockhart | 128/216 |
| 3,276,632 | 10/1966 | Stanzel | 222/83.5 |
| 3,406,872 | 10/1968 | Fiquet et al. | 222/83 |
| 3,508,547 | 4/1970 | Deuschle | 128/269 |
| 3,774,609 | 11/1973 | Schwartzman | 128/269 |
| 3,847,151 | 11/1974 | D'Alessandro | 128/269 |
| 3,876,314 | 4/1975 | Nehring | 401/133 |
| 3,896,808 | 7/1975 | Szpur | 128/269 |

*Primary Examiner*—Aldrich F. Medbery
*Attorney, Agent, or Firm*—Jacox & Meckstroth

[57] ABSTRACT

An elongated tubular container or bag of plastics film material is heat sealed to form a hermetically-sealed container portion for enclosing a predetermined volume of fluid. An elongated handle member of relatively rigid plastics material, extends longitudinaly within the container portion and has one or more pointed tip portions. An end portion of the sealed bag is folded back against the container portion to form a tab portion, and the folded end portion of the bag and the pointed tip portion of the handle member are inserted within a slot formed within a resilient sponge-like swab or applicator. When the projecting tab portion is pulled, the handle member pierces one or more holes within the container portion of the bag so that the fluid may be dispensed into the center portion of the applicator in response to pressure applied to the bag.

21 Claims, 8 Drawing Figures

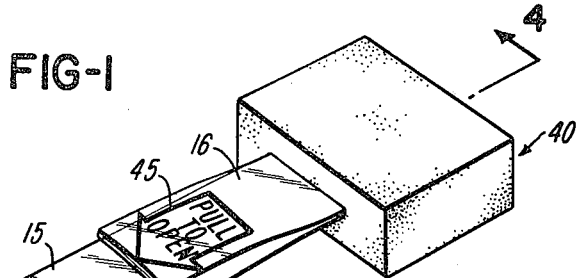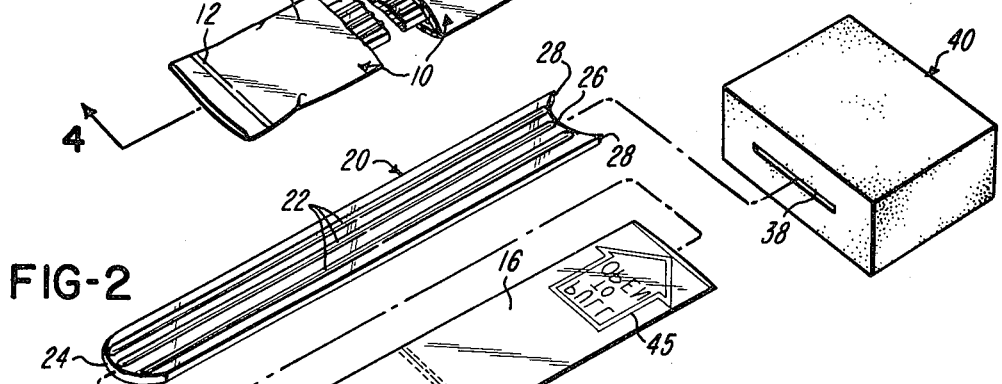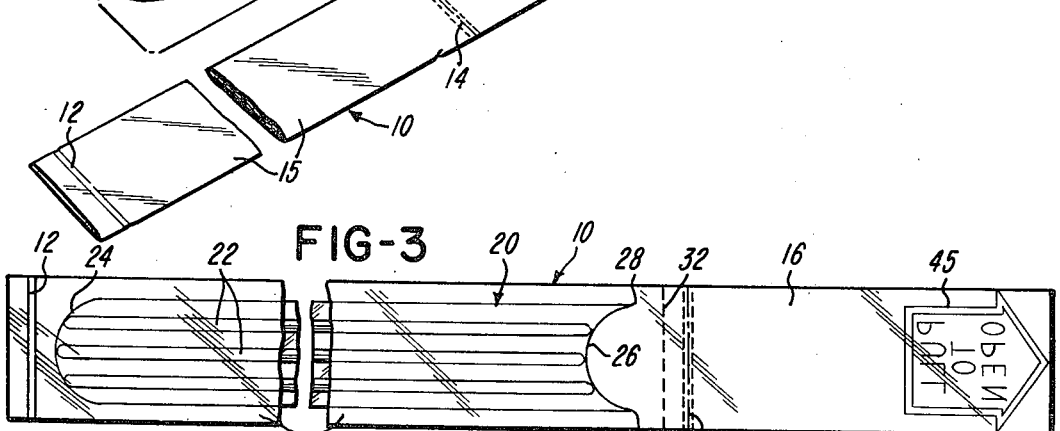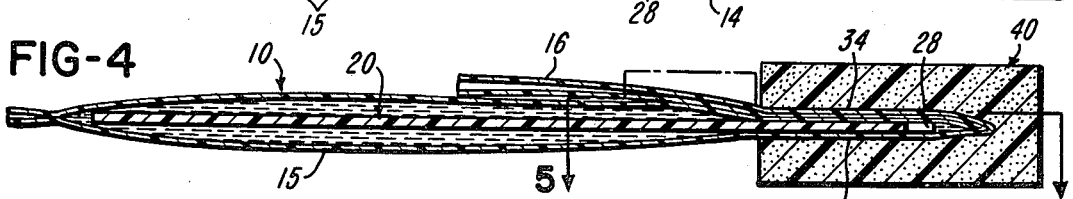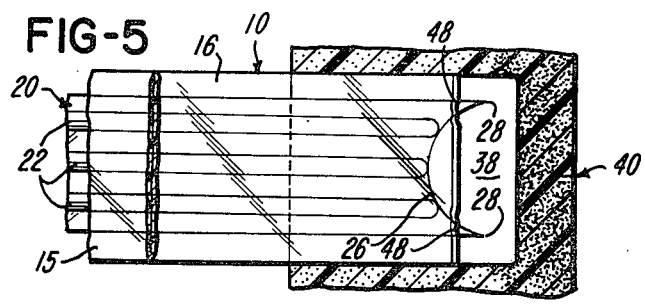

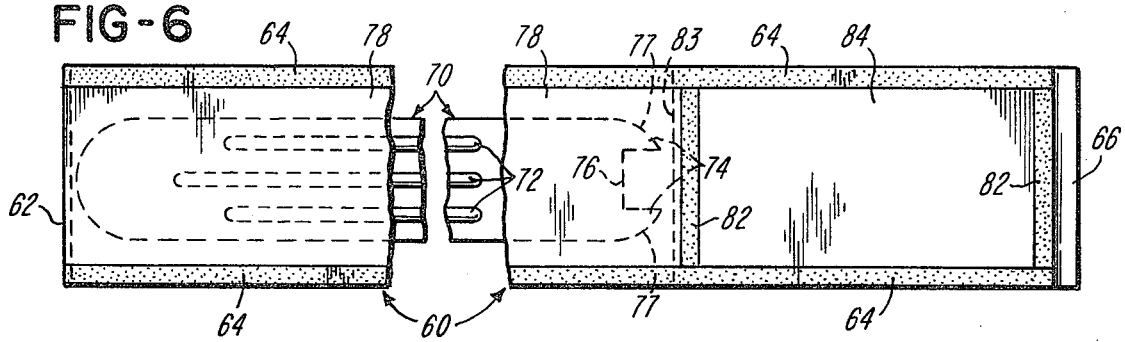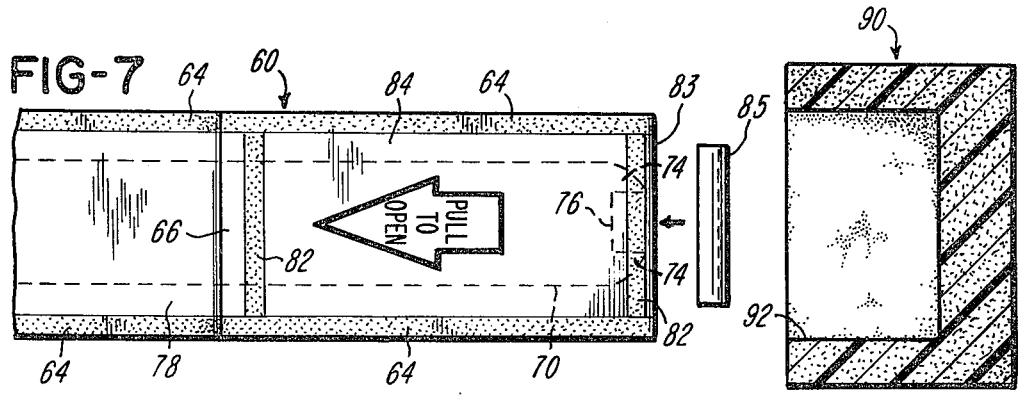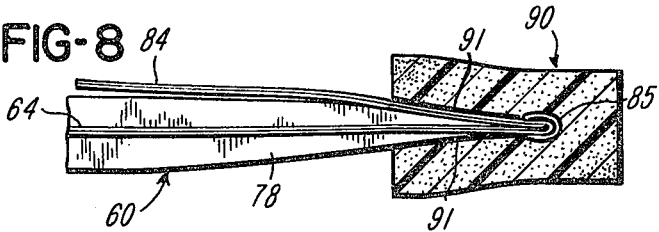

3,981,304

DISPENSING AND APPLICATING DEVICE AND PRODUCTION OF SAME

RELATED APPLICATION

This application is a continuation-in-part of application Ser. No. 486,463, filed July 8, 1974, now issued as U.S. Pat. No. 3,896,808.

BACKGROUND OF THE INVENTION

In preparing a patient for surgery, it is common to apply an iodine base solution to the area where the incision will be made to provide for sterilizing the area. A similar solution may also be used after the surgery is completed for cleaning and sterilizing the skin tissue around the area which has been stitched together. Sometimes, the sterilizing solution is poured into a cup, and a sponge-like swab or applicator, attached to one end of a rigid handle, is used for applying the solution. For example, one such type of applicator is disclosed in U.S. Pat. No. 3,508,547. It has also been found desirable to combine the sponge-like applicator with a container for storing the solution to eliminate the separate handling of the solution and to provide for a more convenient application of the solution. U.S. Pat. No. 3,774,609 discloses such an applicator which provides for applying the solution into the applicating sponge or swab by puncturing holes within the container with prongs projecting from a U-shaped clip extending around the swab.

SUMMARY OF THE INVENTION

The present invention is directed to an improved device for dispensing a solution or fluid into a swab or applicator and which eliminates the need for touching or gripping the applicator when it is desired to dispense a fluid into the applicator. The device of the invention is also economical in construction and is adapted to be produced by substantially automatic machinery. Another feature of the device of the invention is that it provides for controlled dispensing of the fluid into the applicator during use of the device so that the person applying the solution has control over the rate of application. For purpose of the present invention, the term fluid is intended to include any material which flows, including liquids and granular and powder materials.

In accordance with one illustrated embodiment of the invention, an elongated extruded tube of plastics film material is heat sealed at longitudinally spaced intervals to define a container portion, and a predetermined volume of fluid is enclosed within the container along with an elongated handle member formed of a relatively rigid plastics material. The handle member has a pointed end portion, and the bag is folded back upon itself adjacent the pointed end portion of the handle member to form a tab portion. The folded end portion of the bag is coated with adhesive and is inserted into a slot formed within a swab or applicator consisting of a foam-like resilient material. When the projecting tab portion is pulled, the applicator sponge distorts, and the handle member punctures the bag within the applicator. When the tab portion is released, the punctured opening or openings within the bag provide for a flow of the fluid from the bag into the center portion of the applicator in response to the gripping pressure applied to the bag.

Other features and advantages of the invention will be apparent from the following description, the accompanying drawings and the appended claims.

BRIEF DESCRIPTION OF THE DRAWINGS

FIG. 1 is a perspective view of a dispensing and applicating device constructed in accordance with the invention and with a portion broken away;

FIG. 2 is an exploded perspective view illustrating the components of the device shown in FIG. 1;

FIG. 3 is a plan view of the bag with the handle member therein and with a center portion broken away;

FIG. 4 is a slightly enlarged section taken generally on the line 4—4 of FIG. 1;

FIG. 5 is a fragmentary section taken generally on the line 5—5 of FIG. 4;

FIG. 6 is a plan view similar to FIG. 3 and showing a modified form of the bag or container portion of the device;

FIG. 7 is a fragmentary exploded view, in part section, of the modified form of the device; and FIG. 8 is a fragmentary section of the modified form of the device after assembly.

DESCRIPTION OF THE PREFERRED EMBODIMENTS

Referring to FIGS. 1 and 2, an elongated container or bag 10 of flexible thermoplastics film material such as a form of polyethylene, is preferably formed by cutting an extruded tube. The bag 10 has a set of longitudinally spaced heat seals 12 and 14 which define therebetween a container portion 15. The bag 10 also includes a flap or tab portion 16 which is defined between the heat seal 14 and the corresponding end of the bag. While the bag 10 is preferably extruded in the form of a tubular film in order to minimize heat sealed joints, it is to be understood that the bag may be formed by folding a single sheet and heat sealing the folded sheet along one longitudinal edge or by joining two separate film sheets with the heat seals around the entire container portion of the bag. The wall thickness of the bag is within a range of 0.003 and 0.010 inch and preferably on the order of 0.004 inch, and the flexibility of the film enables the bag 10 to collapse from a generally circular cross-sectional configuration to a substantially flat configuration as shown in FIG. 2.

An elongated handle member 20 is formed of a thermoplastics material such as polypropylene and includes a set of longitudinally extending stiffening ribs 22 to provide the handle member 20 with substantial rigidity relative to the flexible film bag 10. One end of the handle member 20 has a rounded or convex surface 24 and the opposite end has a concaved surface 26 which forms a set of sharp pointed tip portions 28. Preferably, the radius of curvature of the surface 26 is the same as that of the surface 24 so that the handle member 20 may be formed by extruding a continuous plastics strip and then die cutting the strip at longitudinally spaced intervals according to the desired length of the handle member 20. The handle member 20 may also be formed by injection molding the plastics material within a corresponding die cavity.

As illustrated in FIGS. 1 and 3, the handle member 20 extends longitudinally within the elongated container portion 15 of the bag 10 so that the pointed tip portions 28 are spaced slightly inwardly from the laterally extending heat seal 14 (FIG. 3). After a predetermined quantity of fluid, for example, an iodine solution is inserted into the container portion 15, the container portion is closed by the heat seal 14 so that the handle member 20 and the fluid are confined within a hermetically sealed chamber defined by the container portion 15. In one sample embodiment of the invention, 10 cc of surgical preparatory solution was sealed within the container portion 15 of the bag 20.

After the container portion of the bag is closed by the heat seal 14, the bag is folded along a fold line 32 (FIG. 3) so that the tab portion 16 extends rearwardly or outwardly adjacent the container portion 15 of the bag 10. A coating of adhesive 34 (FIG. 4) is applied to the outer exposed surfaces of the folded end portion of the bag 20, and the folded end portion of the bag and the corresponding end portion of the handle member 20 are inserted into a slot 38 formed within one longitudinal side of a resilient sponge-like swab or applicator 40. As illustrated, the applicator 40 consists of a rectangularly shaped block or body of polyurethane sponge material. However, the applicator 40 may have other shapes and configurations and may be formed of other materials. As shown in FIG. 4, the slot 38 extends approximately three-quarters of the width of the applicator 40, and the adhesive 34 attaches the outer surface of the tab portion 16 to one side portion of the applicator 40 and the outer surface of the container portion 15 to the other side portion of the applicator 40.

As shown in FIG. 1, the tab portion 16 of the bag 20 is printed with an arrow 45 surrounding the words "PULL TO OPEN". When it is desired to dispense the fluid within the container portion 15 into the center portion of the swab or applicator 40, the return tab portion 16 is simply pulled with one hand in the direction of the arrows 45 while the container portion 15 and the enclosed handle member 20 are being gripped with the other hand. The pulling of the tab portion 16 causes the resilient applicator 40 to distort until the pointed tip portions 28 of the handle member 20 pierce corresponding holes 48 within the bag 20 adjacent the fold line 32. When the tab portion 16 is released, the distorted applicator 40 returns to its normal position shown in FIG. 4, and the pierced holes 48 within the bag 10 are separated from the pointed tip portions 28 of the handle member 20 so that the holes 48 are opened.

A continued pressure applied to the container portion 15 of the bag 10, as a result of the gripping action, is effective to collapse the container portion 15 and thereby displace the fluid through the holes 48 into the center portion of the applicator 40. As the fluid is forced into the applicator 40 while the device is being used with an oscillating painting-like motion, alternating pressures are applied to opposite sides of the container portion 15 of the bag 10 so that the fluid is effectively dispensed or pumped from the container portion 15 into the applicator 40.

Referring to FIGS. 6-8, another form of dispensing and applicating device is constructed similar to the device described above in connection with FIGS. 1-5, but with some modifications. As one modification, the elongated container or bag 60 is formed from a laminated flexible sheet material which includes an inner layer of thermoplastics material such as polyethylene film laminated to a layer of aluminum foil on which is laminated another layer of thermoplastics material such as nylon. The laminated sheet material is folded so that it forms a folded edge 62, and the folded strip or sheet is heat sealed along a pair of parallel spaced longitudinally extending heat seal lines or strips 64 to form an elongated chamber or pouch. One side wall of the container or bag 60 projects beyond the opposing side wall to form a projecting lip portion 66.

An elongated handle member 70 is preferably molded of a substantially rigid thermoplastics material in a manner as mentioned above in connection with the handle member 20, and also includes a plurality of reinforcement or stiffening ribs 72 which terminate short of the opposite ends of the handle member. The handle member 70 also includes a pair of pointed tip portions 74 which are defined by a generally rectangular notch 76 and rounded corner edge surfaces 77. After the handle member 70 and a predetermined quantity of fluid is inserted into the larger container portion 78 of the elongated container or bag 60, the side walls of the bag 60 are heat-sealed along laterally extending parallel lines or strips 82 so that the fluid and the handle member 70 are completely enclosed within a hermetically sealed chamber defined by the container portion 78 of the bag 60.

After the bag 60 is sealed by the heat seal strips 82, the bag is folded along the fold line 83 so that the flap or tab portion 84 overlies the container portion 78 in the same manner as described above in connection with FIG. 3. An elongated U-shaped retainer clip 85 (FIG. 7) is then pressed onto the folded edge portion of the bag 60 to assure that the tab portion 84 lies closely adjacent the container portion 78 and does not spring back. Preferably, the retainer clip 85 is formed by cutting a section from an extrusion of thermoplastics material, and the clip 85 also receives the pointed tip portions 74 of the handle member 70 to form a protector.

An applicator 90 in the form of a block or pad of resilient open cell plastics foam material, is formed with a thin slot 92 in the same manner as the applicator 40 described above is formed with a slot 38. A suitable adhesive 91 is inserted into the slot 92 by means of a rigid tongue which is immersed in the adhesive. The folded end portion of the container or bag 60 and the retainer clip 85 are then inserted into the slot 92. The adhesive coating within the slot 92 forms a bond between the applicator 90 and the adjacent wall surfaces of the container portion 78 and the tab portion 84 of the bag 60. Preferably, the adhesive is inserted into the slot 92 of the applicator 90 rather than applying the adhesive to the tab portion 84 and container portion 78 of the bag 60 in order to assure that the adhesive does not flow between the tab portion and the container portion and bond the two portions together.

The dispensing and applicating device disclosed in FIGS. 6-8 is used in the same manner as the device disclosed in connection with FIGS. 1-5. That is, when it is desired to dispense the fluid from the container portion 78 of the bag 60 into the center portion of the applicator 90, the tab portion 84 is pulled until the pointed tip portions 74 puncture corresponding holes within the outer folded wall of the bag 60 adjacent the fold line 83. The bottom of the notch 76 limits the extent of piercing of the bag by the pointed tip portion 74 and thereby limits the size of the openings or holes punctured within the bag 60. That is, once the folded edge portion of the bag engages the bottom straight edge of the notch 76 in response to pulling the tab portion 84, it is practically impossible to pull the folded edge portion of the bag past the inner edge surface of the notch 76.

From the drawings and the above description, it is apparent that a dispensing device constructed in accordance with the present invention provides desirable features and advantages. For example, the device employs low cost components which may be assembled automatically for high volume production. The handle member 20 or 70 not only serves as a stiffner for the flexible bag 10 or 60, respectively, but also functions to puncture the bag 10 or 60 in the unexposed portion within the center portion of the applicator 40 or 90. It is also apparent that the fluid within the container portion 15 or 78 may be quickly released into the applicator 40 or 90 without touching or gripping the applicator and without bringing the hands or fingers into contact with the fluid. Furthermore, the length and/or width of the container portion 15 or of the bag 10 or 60 may be easily changed if it is desired to change substantially the volume of fluid within the container portion.

As also mentioned above, the configurations of the pointed tip portions 28 and 74 of the handle members 20 and 70, provide for limiting the extent of piercing or puncturing of the bags 10 and 60 so that openings or holes of controlled size are formed. In addition, the outer rounded corner surfaces 77 and/or the retainer clip 85 provide for protecting the piercing tip portions 74 and assure that they do not dig into the resilient applicator 90 or become exposed during applicating. Furthermore, the retainer clip 85 assures that the container or bag 60 remains folded while it is being inserted into the applicator slot 92.

While the applicating devices and the methods of making the same herein described, constitute preferred embodiments of the invention, it is to be understood that the invention is not limited to the precise methods and forms of devices described, and that changes may be made therein without departing from the scope and spirit of the invention as defined in the appended claims.

The invention having thus been described, the following is claimed:

1. A device for dispensing a fluid, comprising a flexible container including a container portion defining a chamber adapted to receive the fluid, a piercing member extending within said chamber and providing said container portion with increased rigidity, means for sealing said container portion to confine the fluid and said piercing member within said chamber, said piercing member including means for piercing at least one hole in said container portion in response to relative movement between said container and said piercing member to provide for dispensing the fluid from said container portion, and said container includes a tab portion projecting from said container portion and adapted to be folded adjacent said piercing means and pulled to effect piercing of said hole by said piercing member.

2. A device as defined in claim 1 including a resilient sponge-like applicator defining a slot receiving said container portion and said tab portion, and means attaching said container to said applicator.

3. A device as defined in claim 2 wherein said attaching means comprises an adhesive within said slot.

4. A device as defined in claim 1 wherein said container and said piercing member are elongated, said sealing means compris a seal extending laterally across the bag, and said piercing means includes a pointed end portion disposed generally adjacent said seal.

5. A device as defined in claim 1 wherein said container is collapsible from an expanded condition to a generally flat condition in response to dispensing the fluid from said container portion by the application of manual pressure on said container.

6. A device as defined in claim 1 wherein said container comprises a multiple layer flexible sheet including a thin layer of plastics material.

7. A device as defined in claim 6 wherein said sheet further includes a metal foil adjacent said layer of thermoplastics material.

8. A device as defined in claim 1 wherein said piercing means of said piercing member comprise at least one pointed tip portion on said piercing member.

9. A device as defined in claim 8 wherein said piercing member includes a plurality of laterally spaced pointed tip portions defining a notch therebetween, and said pointed tip portions have pointed ends disposed laterally inwardly from the outer edge surfaces of said piercing member.

10. A device as defined in claim 1 including a generally U-shaped clip member for retaining said portion in folded relation adjacent said container portion.

11. A device as defined in claim 10 wherein said clip member, said container portion, said tab portion and said piercing member project into a resilient sponge-like applicator.

12. A device for dispensing a fluid, comprising an elongated flexible container including a container portion defining an elongated chamber adapted to receive the fluid, an elongated generally flat piercing member extending within said chamber and providing said container portion with increased rigidity, means for sealing said container portion to confine the fluid and said piercing member within said chamber, said piercing member including at least one pointed tip portion for piercing a hole in said container portion in response to relative movement between said container and said piercing member to provide for dispensing the fluid from said container portion and said container includes a tab portion projecting longitudinally from said container portion and adapted to be folded adjacent said pointed tip portion and pulled to effect piercing of said hole by said piercing member.

13. A device as defined in claim 12 including a resilient sponge-like applicator defining a slot receiving said container portion and said tab portion, and means attaching said container to said applicator.

14. A device as defined in claim 12 wherein said container comprises a multiple layer flexible sheet including a thin layer of plastics material and a layer of metal foil.

15. A device as defined in claim 12 wherein said piercing member includes means adjacent said tip portion for limiting the movement of said container relative to said piercing member when said tab portion is pulled.

16. A method of making a fluid dispensing device, comprising the steps of forming a container of flexible thin wall material, forming a piercing member includng piercing means thereon, inserting said piercing member and a volume of fluid into said container, sealing said container to form a container portion for enclosing said piercing member and fluid, and forming on said container a tab portion projecting from said container portion and adapted to be folded adjacent said piercing means and then pulled to pierce a hole within said chamber portion.

17. A method as defined in claim 16 including the step of forming an applicator from a resilient body of sponge-like material, forming a slot within said applicator, and inserting said container portion and a folded-over said tab portion into said slot.

18. A method as defined in claim 17 wherein said container portion and said folded-over tab portion are attached by adhesive to said resilient body within said slot.

19. A method as defined in claim 16 wherein said container is formed of a multiple layer flexible sheet material including a layer of metal foil and a layer of thermoplastics material.

20. A method as defined in claim 16 wherein said handle member is formed generally flat and with a plurality of pointed tip portions.

21. A method as defined in claim 16 including the step of inserting a generally U-shaped clip member onto said container portion and said tab portion after folding said tab portion over onto said container portion, and mounting a resilient body of sponge-like material onto said clip member and the adjacent said portions of said container.

* * * * *